(12) United States Patent
Zhang et al.

(10) Patent No.: US 9,290,524 B2
(45) Date of Patent: Mar. 22, 2016

(54) METHODS FOR PRODUCING FUNCTIONALIZED GRAPHENES

(71) Applicant: WASHINGTON STATE UNIVERSITY RESEARCH FOUNDATION, Pullman, WA (US)

(72) Inventors: Jinwen Zhang, Pullman, WA (US); Yu Fu, Pullman, WA (US)

(73) Assignee: Washington State University, Pullman, WA (US)

(*) Notice: Subject to any disclaimer, the term of this patent is extended or adjusted under 35 U.S.C. 154(b) by 249 days.

(21) Appl. No.: 13/837,904

(22) Filed: Mar. 15, 2013

(65) Prior Publication Data

US 2014/0275597 A1 Sep. 18, 2014

(51) Int. Cl.
C07F 7/10 (2006.01)
C07F 7/18 (2006.01)

(52) U.S. Cl.
CPC .................................. C07F 7/1896 (2013.01)

(58) Field of Classification Search
CPC ..................................................... C07F 7/1896
USPC ......................................................... 556/418
See application file for complete search history.

(56) References Cited

U.S. PATENT DOCUMENTS

2011/0319554 A1 12/2011 Frazier et al.
2012/0261612 A1 10/2012 Suh et al.

FOREIGN PATENT DOCUMENTS

WO WO2011/159922 A2 12/2011
WO WO 2011159922 A2 * 12/2011 ............. B82Y 30/00
WO WO 2012159051 A2 * 11/2012

OTHER PUBLICATIONS

Zhao et al. J. Mater. Chem., 2010, 20, 5817-5819.*
Bauhofer et al., A review and analysis of electrical percolation in carbon nanotube polymer composites, *Composites Science and Technology* (2008), pp. 1-26.
Hernandez et al., High-yield production of graphene by liquid-phase exfoliation of graphite, *Nature Nanotechnology* (Aug. 10, 2008), 3:563-568.
Albert et al., Characterization of bonded phases by solid-state NMR spectroscopy, *Journal of Chromatography A* (May 17, 1991), 544:345-370 (Abstract).
Bansal et al., Quantitative equivalence between polymer nanocomposites and thin polymer films, *Nature Materials* (Aug. 7, 2005), 4:693-698 (Abstract).
Che et al., A new approach to fabricate graphene nanosheets in organic medium: combination of reduction and dispersion, *Journal of Materials Chemistry* (Jan. 14, 2010), 20(9):1722-1727 (Abstract).
Chen et al., Preparation of graphene by the rapid and mild thermal reduction of graphene oxide induced by microwaves, *Carbon* (Apr. 2010), 48(4):1146-1152 (Abstract).
Colomban et al., Raman and IR micro-analysis of high performance polymer fibres tested in traction and compression, *Composites Science and Technology* (Jan. 2009), 69(1):10-16 (Abstract).
Compton et al., Graphene Oxide, Highly Reduced Graphene Oxide, and Graphene: Versatile Building Blocks for Carbon-Based Materials, *Small* (Mar. 11, 2010), 6(6):711-723 (Abstract).
Ferrari et al., Interpretation of Raman spectra of disordered and amorphous carbon, *Phys. Rev. B* (May 15, 2000), 61(20):14095-14107 (Abstract).
Ferrari et al., Raman Spectrum of Graphene and Graphene Layers, *Phys. Rev. B* (Oct. 30, 2006), 97(18):187401-187404 (Abstract).
Fu et al., Ionic Liquid-Assisted Exfoliation of Graphene Oxide for Simultaneous Reduction and Functionalization to Graphenes with Improved Properties, *J. Mater. Chem. A* (2013), 1:2663-2674.
Fukushima et al., Molecular Ordering of Organic Molten Salts Triggered by Single-Walled Carbon Nanotubes, *Science* (Jun. 27, 2003), 300(5628):2072-2074 (Abstract).
Fukushima et al., Ionic Liquids for Soft Functional Materials with Carbon Nanotubes, *Chemistry—A European Journal* (May 22, 2007), 13(18):5048-5058 (Abstract).
Guo et al., Constructing Carbon Nanotube/Pt Nanoparticle Hybrids Using an Imidazolium-Salt-Based Ionic Liquid as a Linker, *Advanced Materials* (Jan. 4, 2010), 22(11):1269-1272 (Abstract).
Huddleston et al., Room temperature ionic liquids as novel medial for 'clean' liquid-liquid extraction, *Chemical Communications* (1998), 16:1765-1766 (Abstract).
Hummers et al., Preparation of Graphitic Oxide, *J. Am. Chem. Soc.* (Mar. 1958), 80(6):1339 (Abstract).
Jeong et al., Thermal stability of graphite oxide, *Chemical Physics Letters* (Mar. 5, 2009), 470(4-6):255-258 (Abstract).
Jeong et al., Evidence of Graphitic AB Stacking Order of Graphite Oxides, *J. Am. Chem. Soc.* (Jan. 8, 2008), 130(4):1362-1366 (Abstract).
Jia et al., Carbon nanotube/gold nanoparticles/polyethylenimine-functionalized ionic liquid thin film composites for glucose biosensing, *Biosensors and Bioelectronics* (Dec. 1, 2008), 24(4):945-950 (Abstract).
Jin et al., Mechanically Assisted Exfoliation and Functionalization of Thermally Converted Graphene Sheets, *Chem. Mater.* (Jun. 29, 2009), 21:3045-3047.
Lei et al., Hydrolysable tannin as environmentally friendly reducer and stabilizer for graphene oxide, *Green Chemistry* (May 17, 2011), 13(7):1655-1658 (Abstract).
Lerf et al., Structure of Graphite Oxide Revisited, *J. Phys. Chem B.* (May 13, 1998), 102(23):4477-4482 (Abstract).
Li et al., Processable aqueous dispersions of graphene nanosheets, *Nature Nanotechnology* (Jan. 27, 2008), 3:101-105 (Abstract).
Li et al., Oxygen-Driven Unzipping of Graphitic Materials, *Phys. Rev. Lett.* (May 2, 2006), 96(17):176101-176104 (Abstract).
Liu et al., One-Step Ionic-Liquid-Assisted Electrochemical Synthesis of Ionic-Liquid-Functionalized Graphene Sheets Directly from Graphite, *Advanced Functional Materials* (May 5, 2008), 18(10):1518-1525 (Abstract).

(Continued)

*Primary Examiner* — Porfirio Nazario Gonzalez
*Assistant Examiner* — Kofi Adzamli
(74) *Attorney, Agent, or Firm* — Pepper Hamilton LLP

(57) ABSTRACT

Methods for producing functionalized graphene from graphite oxide or graphite are disclosed in which ionic liquids are used as a reaction medium to promote chemical functionalization of the graphene through electrochemically interacted exfoliation of graphene sheets.

26 Claims, 4 Drawing Sheets

(56) References Cited

OTHER PUBLICATIONS

Lu et al., One-Pot Synthesis of Fluorescent Carbon Nanoribbons, Nanoparticles, and Graphene by the Exfoliation of Graphite in Ionic Liquids, *ACS Nano* (Aug. 5, 2009), 3(8):2367-2375 (Abstract).
Luo et al., Evaluation Criteria for Reduced Graphene Oxide, *J. Phys. Chem. C.* (May 19, 2011), 115(23):11327-11335 (Abstract).
Mermin, Crystalline Order in Two Dimensions, *Phys. Rev.* (Dec. 1968), 176(1):250-254 (Abstract).
Meyer et al., The structure of suspended graphene sheets, *Nature* (Mar. 1, 2007), 446:60-63 (Abstract).
Meyer et al., On the roughness of single- and bi-layer graphene membranes, *Solid State Communications* (Jul. 2007), 143(1-2):101-109 (Abstract).
Moon et al., Reduced graphene oxide by chemical graphitization, *Nature Communications* (Sep. 21, 2010), 1(73) (Abstract).
Novoselov et al., Electric Field Effect in Atomically Thin Carbon Films, *Science* (Oct. 22, 2004), 306(5696):666-669 (Abstract).
Nuvoli et al., High concentration few-layer graphene sheets obtained by liquid phase exfoliation of graphite in ionic liquid, *Journal of Materials Chemistry* (Dec. 20, 2010), 21(10):3428-3431 (Abstract).
Paredes et al., Graphene Oxide Dispersions in Organic Solvents, *Langmuir* (Aug. 29, 2008), 24(19):10560-10564 (Abstract).
Park et al., Aqueous Suspension and Characterization of Chemically Modified Graphene Sheets, *Chem. Mater.* (Oct. 22, 2008), 20(21):6592-6594 (Abstract).
Peng et al., Simultaneous Reduction and Surface Functionalization of Graphene Oxide by Natural Cellulose with the Assistance of the Ionic Liquid, *J. Phys. Chem. C.* (Jul. 9, 2012), 116(30):16294-16299 (Abstract).
Pham et al., Chemical functionalization of graphene sheets by solvothermal reduction of a graphene oxide suspension in N-methyl-2-pyrrolidone, *Journal of Materials Chemistry* (Dec. 20, 2010), 21(10):3371-3377 (Abstract).
Pringle et al., Conducting Polymers with Fibrillar Morphology Synthesized in a Biphasic Ionic Liquid/Water System, *Macromolecules* (Mar. 22, 2007), 40(8):2702-2711 (Abstract).
Putz et al., Elastic modulus of single-walled carbon nanotube/poly(methyl methacrylate) nanocomposites, *Journal of Polymer Science Part B: Polymer Physics* (May 3, 2004), 42(12):2286-2293 (Abstract).
Putz et al., The role of interfacial interactions in the dynamic mechanical response of functionalized SWNT-PS nanocomposites, *Polymer* (Jun. 4, 2007), 48(12):3540-3545 (Abstract).
Rafiee et al., Wetting transparency of graphene, *Nature Materials* (Jan. 22, 2012), 11:217-222 (Abstract).
Ramanathan et al., Functionalized graphene sheets for polymer nanocomposites, *Nature Nanotechnology* (May 11, 2008), 3:327-331 (Abstract).
Ramanathan et al., Functionalized SWNT/polymer nanocomposites for dramatic property improvement, *Journal of Polymer Science Part B: Polymer Physics* (Jul. 12, 2005), 43(17):2269-2279 (Abstract).
Safavi et al., High electrocatalytic effect of palladium nanoparticle arrays electrodeposited on carbon ionic liquid electrode, *Electrochemistry Communications* (Aug. 2007), 9(8):1963-1968 (Abstract).
Salgado et al., Targeting Chemical Morphology of Graphene Oxide for Self-Assembly and Subsequent Templating of Nanoparticles: A Composite Approaching Capacitance Limits in Graphene, *J. Phys. Chem. C.* (May 14, 2012), 116(22):12124-12130 (Abstract).
Snook et al., Co-deposition of conducting polymers in a room temperature ionic liquid, *Journal of Materials Chemistry* (May 13, 2009), 19(24):4248-4254 (Abstract).
Stankovich et al., Stable aqueous dispersions of graphitic nanoplatelets via the reduction of exfoliated graphite oxide in the presence of poly(sodium 4-styrenesulfonate), *Journal of Materials Chemistry* (Nov. 21, 2005), 16(2):155-158 (Abstract).
Stankovich et al., Graphene-based composite materials, *Nature* (Jul. 20, 2006), 442:282-286 *Nature* (Jul. 20, 2006), 442:282-286.
Stankovich et al., Synthesis of graphene-based nanosheets via chemical reduction of exfoliated graphite oxide, *Carbon* (Mar. 6, 2007), 45:1558-1565.
Szabo et al., Evolution of Surface Functional Groups in a Series of Progressively Oxidized Graphite Oxiders, *Chem. Mater.* (May 4, 2006), 18(11):2740-2749 (Abstract).
Teng et al., Thermal conductivity and structure of non-covalent functionalized graphene/epoxy composites, *Carbon* (Dec. 2011), 49(15):5107-5116 (Abstract).
Wang et al., Direct exfoliation of natural graphite into micrometer size few layers graphene sheets using ionic liquids, *Chemical Communications* (May 19, 2010), 46(25):4487-4489 (Abstract).
Xiao et al., Characterization of hydrophobic ionic liquid-carbon nanotubes-gold nanoparticles composite film coated electrode and the simultaneous voltammetric determination of guanine and adenine, *Electrochimica Acta* (Nov. 1, 2008), 53(26):7781-7788 (Abstract).
Xu et al., Flexible Graphene Films via the Filtration of Water-Soluble Noncovalent Functionalized Graphene Sheets, *J. Am. Chem. Soc.* (Apr. 10, 2008), 130(18):5856-5857 (Abstract).
Xu et al., Sonochemical Preparation of Functionalized Graphenes, *J. Am. Chem. Soc.* (May 23, 2011), 133:9148-9151.
Zhou et al., Dispersion of graphene sheets in ionic liquid [bmim][$PF_6$] stabilized by an ionic liquid polymer, *Chem. Commun.* (Dec. 1, 2009), 46(3):386-388 (Abstract).

\* cited by examiner

METHODS FOR PRODUCING FUNCTIONALIZED GRAPHENES

BACKGROUND

Graphene, single-layer sheets of pure carbon with the atoms arranged in a hexagonal pattern, is relatively novel as a material of broad interest and potential. Graphene is one of the thinnest, strongest, and stiffest materials known, and is also an excellent conductor of both heat and electricity. Graphene sheets are, however, insoluble in many common organic solvents and indispersible in many polymers without further treatment of the graphene.

For many applications, a simple and facile preparation of graphene dispersions in organic media is a desirable prerequisite for the development of scalable solvent-assisted graphene processing, including surface spin-coatings, inkjet-printing on plastic substrates, graphene films or papers, and conducting displays for applications in nanoelectronics, nanophotonics, electric devices, and sensors. It is also desirable to have the ability to homogenously disperse graphene in polymers, and to achieve good affinity with the polymers for the development of applications such as graphene-based polymer composites and active graphene layers for organic electronic elements. A dispersion of graphene oxide or graphene at as low as 0.05 wt % in a polymer matrix could result in exceptional enhancements in electrical conductivity and mechanical properties.

One general method for formation of graphene is commonly referred to as a "bottom-up" production in which graphene may be obtained by chemical vapor deposition, or from micro-mechanical cleavage of graphite wherein single graphene layers are pulled off the graphite. An alternate approach, referred to as a "top-down" approach, involves the oxidation of graphite to form graphite oxide, followed by exfoliation and reduction of the graphite oxide. However, the toxic reducing agent hydrazine is commonly used in this process, and may result in incompletely exfoliated graphene sheets which cannot effectively interact with the host media. In addition, the exfoliated sheets may tend to restack or even reform graphite after reduction has taken place.

Cost-effective and mass production strategies for simple and facile exfoliation and effective reduction and surface modification of graphene sheets are desirable for improved top-down preparations.

SUMMARY

In one aspect, the application provides methods and systems for producing functionalized graphene. An essentially one-step approach, performed with an ionic liquid, allows for an electrochemically interacted exfoliation of graphene sheets from graphite oxide along with reduction and functionalization. In some cases, the exfoliation, reduction, and functionalization can take place essentially simultaneously. In addition, no additional stabilizer or modifier is needed to stabilize the resulting processable functionalized graphene dispersions.

In an embodiment, a method for producing functionalized graphene includes contacting graphite oxide with at least one functionalizing compound in the presence of at least one first ionic liquid at a pressure, temperature, and for a period of time to exfoliate, reduce and functionalize the graphite oxide to produce functionalized graphene.

In a further embodiment, a functionalized graphene may be produced by a method that includes contacting graphite oxide with at least one functionalizing compound in the presence of at least one first ionic liquid at a pressure, temperature, and for a period of time to exfoliate, reduce and functionalize the graphite oxide.

In another aspect, reaction compositions for producing functionalized graphene are provided. In one embodiment, the composition includes graphene oxide, a first ionic liquid, and a functionalizing compound. The composition may further include a solvent, a catalyst, or both.

In a further aspect, functionalized graphene and compositions including functionalized graphene are provided. In one embodiment, the functionalized graphene include a graphene moiety functionalized with at least one silane moiety. The graphene moiety may be covalently linked with the silane moiety through a carboxylate group. The graphene moiety may further include peroxide groups. The silane moiety may include an amino group, such as a primary amine group.

DETAILED DESCRIPTION

Figure 1:
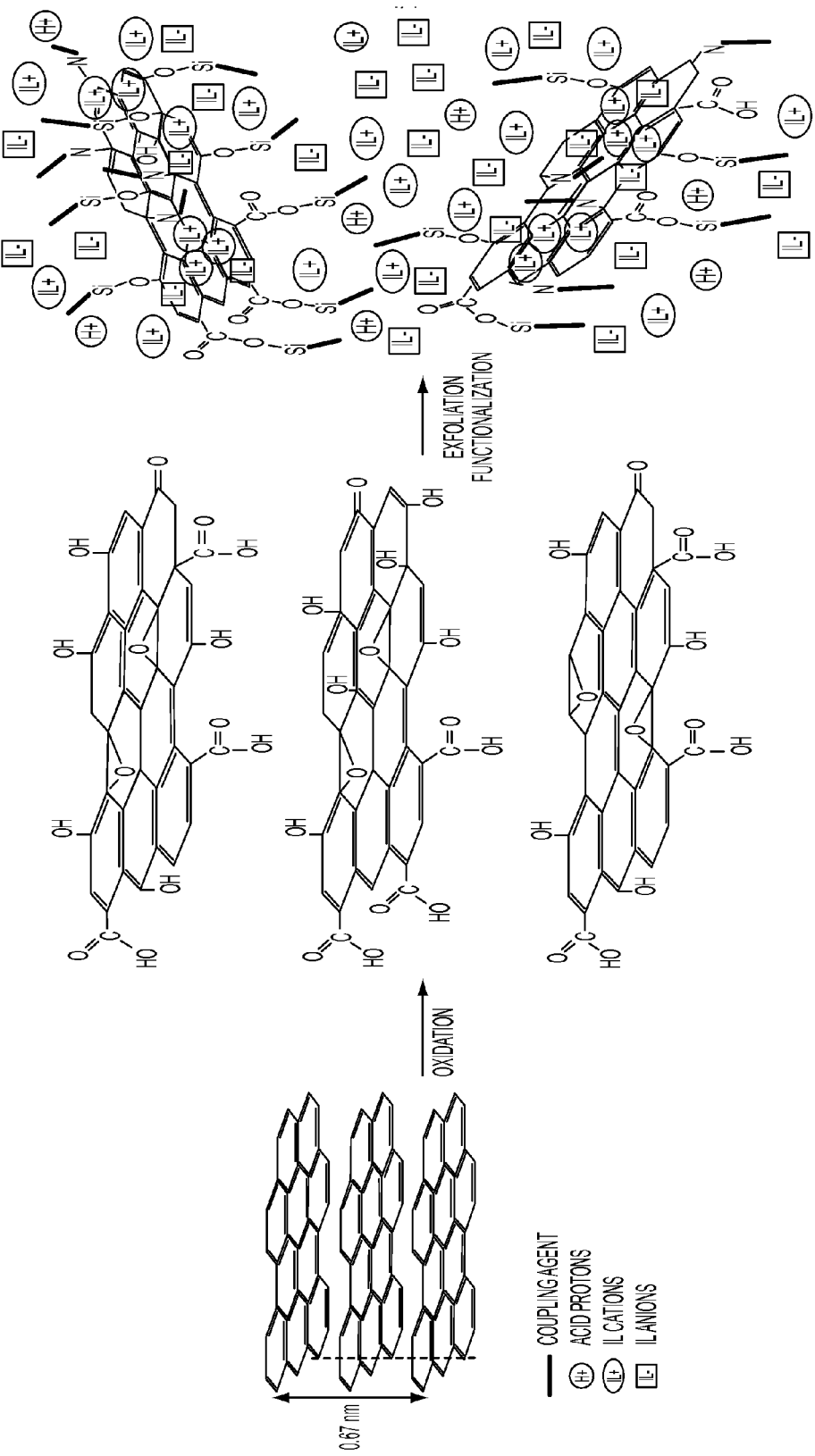
FIG. 1 depicts a representative reaction process for producing functionalized graphene from graphite according to an embodiment.

Exfoliation and dispersion of individual graphene sheets are significant technological challenges in the preparation and processing of graphene for its desired end applications. In contrast to pristine graphite, graphene sheets derived from graphite oxide carry hydroxyl and epoxide functional groups on their basal planes, in addition to carbonyl and carboxyl groups at the sheet edges. The abundant oxygen-containing functional groups attached on the graphitic surfaces of graphite oxide can make the graphite oxide thermally unstable and hydrophilic in nature. Some oxygen-containing functional groups can serve as reactive sites for chemical modifications.

By functionalizing graphene with selective organic moieties, the resulting graphene can be made organophilic and may be able to couple with certain polymers, thereby facilitating the translation of individual graphene properties to the final products. Furthermore, agglomeration normally encountered in most carbon nanotubes can be reduced largely or even prevented completely by surface modification. Therefore, the inherent characteristics of single layer graphene can be maintained. Although the chemically modified graphene nanosheets may be less conductive than pristine graphene layers, such a reduction is anticipated to be offset or even surpassed by the enhancement of the conductive properties resulted from the improved dispersion of the individual graphene layers in a matrix or solvents.

Ionic liquids are extensively used as green reaction media in the synthesis of conducting polymers and nanoparticles due to their low vapor pressures and wide electrochemical potential windows. Ionic liquids have been determined to be effective media for the exfoliation of graphene sheets from graphite, and, along with attached functional groups on graphene oxide, provide sufficient electrostatic repulsion to overcome the intersheet van der Waals attractions to allow the electrostatic and steric stabilization of functionalized graphene.

It has been determined that the use of ionic liquids as a processing aid and reaction medium promotes chemical functionalization of graphene through the electrochemically interacted exfoliation of graphene sheets. In an embodiment, functionalized graphene may be produced by contacting graphite oxide with at least one functionalizing compound in the presence of at least one ionic liquid at a pressure, temperature, and for a period of time to exfoliate, reduce and functionalize the graphite oxide. In a further embodiment, the graphite oxide precursor for the functionalized graphene may be produced by comminuting graphite in the presence of an ionic liquid to produce pre-treated graphite, and then converting the pre-treated graphite into graphite oxide.

The ionic liquid used in the exfoliation, reduction and functionalizing, may be the same as, or different from the ionic liquid used in the comminution. The ionic liquid may be a single ionic liquid, or a combination of two or more ionic liquids. The ionic liquid may be an ionic liquid which is capable of providing ions that may intercalate between the layers of the graphite, or graphite oxide, to enhance exfoliation. Some examples of ionic liquids include: imidazolium type ionic liquids, phosphonium type ionic liquids, 1-butyl-2,3-dimethylimidazolium chloride, 1-butyl-2,3-dimethylimidazolium tetrafluoroborate, 1-butyl-2,3-dimethylimidazolium hexafluorophosphate, 1-butyl-3-methylimidazolium acetate, 1-butyl-3-methylimidazolium bis(trifluoromethylsulfonyl)imide, 1-butyl-3-methylimidazolium bromide, 1-butyl-3-methylimidazolium dibutyl phosphate, 1-butyl-3-methylimidazolium methanesulfonate, 1-butyl-3-methylimidazolium tetrafluoroborate, 1-ethyl-2,3-dimethylimidazolium tetrafluoroborate, 1-ethyl-2,3-dimethylimidazolium chloride, 1-ethyl-2,3-dimethylimidazolium hexafluorophosphate, 1-ethyl-3-methylimidazolium bromide, 1-ethyl-3-methylimidazolium chloride, 1-ethyl-3-methylimidazolium hexafluorophosphate, 1-ethyl-3-methylimidazolium trifluoromethanesulfonate, 1-hexyl-3-methylimidazolium chloride, 1-hexyl-3-methylimidazolium hexafluorophosphate, 1-hexyl-3-methylimidazolium tetrafluoroborate, 1-hexyl-3-methylimidazolium trifluoromethansulfonate, trihexyltetradecylphosphonium decanoate, trihexyltetradecylphosphonium bis(2,4,4-trimethylpentyl)phosphinate, and trihexyltetradecylphosphonium dicyanamide, or any combination thereof.

While many sources of graphite may be used, the most common source of graphite for chemical reactions, including oxidation, is flake graphite, which is a naturally occurring mineral that is purified to remove heteroatomic contamination. Flake graphite contains numerous, localized defects in its π-structure that may serve as seed points for the oxidation process. To prepare graphite oxide, the size of the graphite particles may be reduced if desired, for example, by grinding with a mortar and pestle, or by any other type of comminution, for example, a ball mill. The addition of an ionic liquid to the graphite prior to or during comminuting may assist in breaking up graphite as the cations intercalate between the layers of the graphite and possibly become adsorbed on the graphite layers, forming a charged diffuse layer. These charged layers may produce the Coulomb repulsion forces between charged graphene sheets to help overcome van der Waals attractions between the layers to at least open the spacing between the layers and inhibit re-stacking. In this manner, the achieved graphite oxide contains numerous, localized defects in its π-structure that may serve as seed points for further processing. The grinding, or comminution, may be performed until the graphite particles have an average size of less than about 50 microns or other desired average size.

The resulting gel-like paste may be washed with water and may be filtered and dried to produce a graphite powder. Drying may be performed at room temperature or at an elevated temperature. Graphite powder may be oxidized by generally any method, with some common methods including the Brodie method, the Staudenmeier method, and the Hummer method. The Brodie and Staudenmeier methods both involve the addition of potassium chlorate to a slurry of graphite in nitric acid. The Staudenmeier method differs from Brodie by the addition of the potassium chlorate in aliquots, instead of all at once, and also include the addition of concentrated sulfuric acid to increase the acidity. The Hummers method uses a combination of potassium permanganate and sulfuric acid, with the active species being diamanganese heptoxide that is formed during the reaction between the potassium permanganate and the sulfuric acid. A more specific example is presented below in Example 1 for an embodiment that uses a modified Hummers method. As shown in FIG. 1, the oxidation reactions may result in any of various oxide-containing species, hydroxyls, carboxyls, epoxides, ketones, and lactones, for example, on the graphite oxide. Functionalization may occur at essentially any or all of the oxygen sites.

The resultant graphite oxide may be washed with water and suspended in an aqueous mixture. The mixture may be subjected to dialysis to remove any residual salts and acids, and the graphite oxide may be stored as an aqueous dispersion or may be freeze dried.

As also represented in FIG. 1, functionalization of the graphite oxide may be performed with essentially a single reaction mixture wherein the graphite oxide may be contacted with at least one functionalizing compound in the presence of at least one ionic liquid so that exfoliation of the graphite occurs along with reduction and functionalization. A reaction composition for producing functionalized graphene may include graphene oxide, a first ionic liquid, and a functionalizing compound.

The ionic liquid may be any one or more of the previously mentioned ionic liquids to provide ions to intercalate between the graphite oxide layers and help exfoliate the layers.

The functionalizing compound may be a coupling agent. Coupling agents may be any compounds which have at least two reactive groups, thereby allowing the compounds to react with and 'couple' two components. Coupling agents are often used to join two immiscible components, or alter the polarity of a surface, thereby allowing dispersion of one material into another, previously immiscible material. In an embodiment, the coupling agent may therefore be a monomeric species having at least two functional groups, wherein the coupling agent is chosen, or configured, so that one of the functional groups is able to react with the oxidized graphite to attach the functional group to the graphite, and the other functional group is selected for another designated purpose, such as to provide dispersion in a polymer.

Some examples of coupling agents include, but are not limited to, silicon-based coupling agents and germanium based-coupling agents. In an embodiment, the functionalizing compound may be a silicon-based coupling agent, a germanium-based coupling agent, or a combination thereof. In embodiments, the functionalizing compound may be (3-aminopropyl)trimethoxysilane, 3-glycidoxypropyldimethoxymethylsilane, (3-mercaptopropyl)trimethoxysilane, 3-(triethoxysilyl)propyl isocyanate, N1-(3-trimethoxysilylpropyl) diethylenetriamine, or N[3-(trimethoxysilyl)propyl] ethylenediamine, or any combination thereof.

With silane coupling agents, functionalization of graphene oxide may occur between the —COOH and silanol upon hydrolysis of the silane coupling agents. In addition, functionalization may also occur between —OH of graphene oxide and —$NH_2$, and epoxide of graphene oxide and —$NH_2$. In an embodiment wherein 3-aminopropyl triethoxysilane is used as the functionalizing compound, the 3-aminopropyl triethoxysilane may undergo hydrolysis prior to functionalization, followed by condensation reactions with the hydroxyl and carboxyl groups. In addition, some 3-aminopropyl triethoxysilane molecules may cross-react with other 3-aminopropyl triethoxysilane molecules during the functionalization. A representative illustration of graphene functionalized with 3-aminopropyl triethoxysilane is depicted in FIG. 2.

Figure 2:
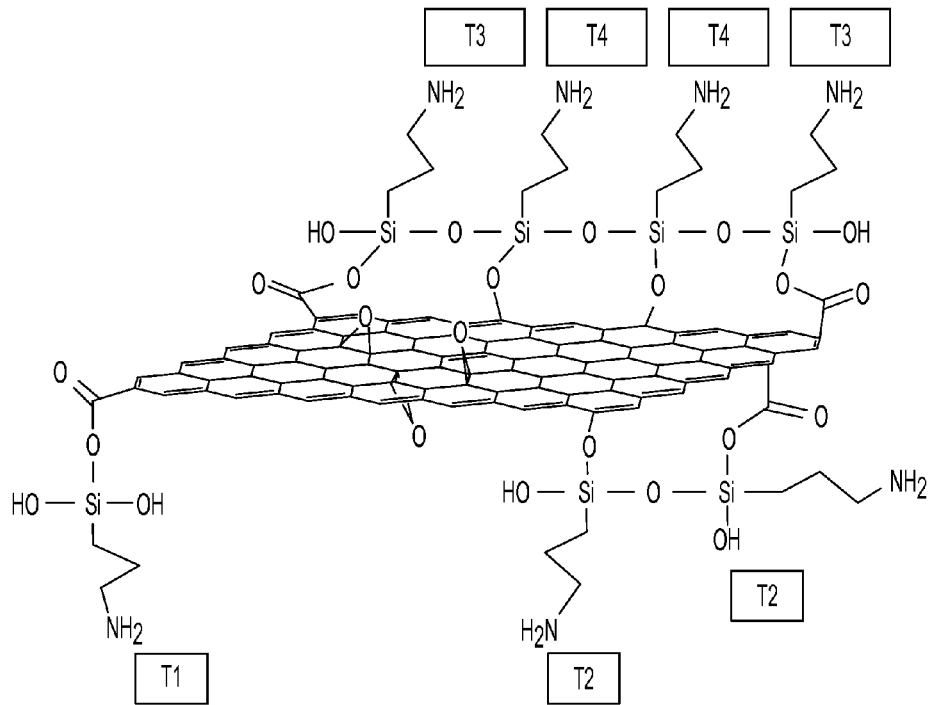
FIG. 2 depicts a representative view of functionalized graphene according to an embodiment.

As shown in the representative embodiment of FIG. 2, a functionalized graphene may be functionalized with at least one silane moiety, wherein the graphene moiety is covalently linked with the silane moiety through carboxylate groups. As shown, some of the silane moieties may be covalently cross-linked with at least one other of the silane moieties by a siloxane bond. As represented by the designations of T1-T4 in FIG. 2 (correlated further below with the spectra depicted in FIGS. 4a and 4b), several different configurations of cross-linked silane moieties may form on the graphene.

As depicted in the embodiment of FIG. 2, the reduced and functionalized graphene may have epoxide groups, and the silane moieties may have amino groups and hydroxyl groups. The amino groups may be primary amino groups.

In an embodiment, the graphite oxide may be contacted with at least one functionalizing compound in the presence of at least one ionic liquid and at least one solvent, wherein the solvent may provide a media for assisting hydrolysis of the functionalizing compounds. A reaction compositions for producing functionalized graphene may include graphene oxide, a first ionic liquid, a functionalizing compound and a solvent. In an embodiment, the ionic liquid and the solvent may be combined together to form a liquid mixture, and the graphite oxide may be deposited into the liquid mixture. In embodiments, the solvent may be water, toluene, dimethylformamide, xylene, ethanol, or any combination thereof.

In an embodiment, the graphite oxide may be contacted with at least one functionalizing compound in the presence of at least one ionic liquid and at least one catalyst, wherein the catalyst may be an acid or base provided to assist in hydrolysis of the functionalizing compound. The presence of acid protons may also enhance exfoliation by intercalation of the acids between the layers to decouple the electronic behavior of the layers and separate the layers. A reaction compositions for producing functionalized graphene may include graphene oxide, a first ionic liquid, a functionalizing compound and a catalyst.

In an embodiment, the catalyst may be at least one acid. The acid may be lactic acid, acetic acid, formic acid, citric acid, oxalic acid, uric acid, propionic acid, butyric acid, sorbic acid, tartaric acid, malonic acid, malic acid, maleic acid, succinic acid, fumaric acid, hydrochloric acid, nitric acid, phosphoric acid, or any combination thereof. The pH of the resultant solution may be adjusted to be about 4 to about 5.

In an embodiment, the graphite oxide may be contacted with at least one functionalizing compound in the presence of at least one ionic liquid, at least one catalyst, and at least one solvent. A reaction compositions for producing functionalized graphene may include graphene oxide, an ionic liquid, a functionalizing compound, a catalyst and a solvent. The liquid components may be combined to produce a solvent mixture or solvent solution, and the graphite oxide may be deposited into the solvent solution or solvent mixture to produce a graphite oxide-solvent mixture. Exfoliation of the graphite oxide occurs as ions intercalate between the layers of the graphite oxide and lift off layers to produce graphene oxide. The exfoliation optionally may be enhanced by sonicating the mixture.

The graphene oxide may be refluxed at a temperature, pressure, and for a period of time to allow reduction and functionalization to occur. In an embodiment, the temperature may be at least about 25° C. In an embodiment, the pressure may be at least about ambient atmospheric pressure. In an embodiment, the period of time may be at least about 0.5 hours. In further embodiments, the temperature may be about 25° C. to about 180° C., the pressure may be about 0.1 MPa to about 1.1 MPa, and the period of time may be about 0.5 hours to about 72 hours.

The resulting functionalized graphenes may be filtered and washed with solvents, such as ethanol, water, or a combination of ethanol and water. The functionalized graphenes may be freeze-dried for storage.

Chemical structures of the prepared graphene oxide (GO) and subsequently functionalized graphene (functionalized with 3-aminopropyl triethoxysilane (APS)) were verified by Fourier transform infrared (FT-IR), X-ray photoelectron spectroscopy (XPS), and $_{29}Si$ solid-state nuclear magnetic resonance (NMR). To determine the formation of covalent bonds between 3-aminopropyl triethoxysilane (APS) and GO, Fourier transform infra-red (FT-IR) and $_{29}Si$ solid state nuclear magnetic resonance (NMR) measurements were performed on the GO and the functionalized graphene.

The FT-IR characteristic peaks of GO (FIG. 3) appeared at 1725 $cm^{-1}$ (C=O stretching vibration), 1626 $cm^{-1}$ (aromatic ring C=C), 1358 $cm^{-1}$ (carboxyl C—OH stretching), 1214 $cm^{-1}$ (epoxide/ether C—O), and 1054 $cm^{-1}$ (alkoxy/alkoxide C—O stretches). Additionally, the wide peak appearing at 3300-3400 $cm^{-1}$ is due to the hydroxyl groups. Compared to GO, the functionalized GO under the aid of the IL (GO-APS-IL) displayed some new peaks corresponding to —NH (3351 $cm^{-1}$), —CH (2927 $cm^{-1}$), —$CH_2$ (2859 $cm^{-1}$), —$NH_2$ (1578 $cm^{-1}$), C—N (1218 $cm^{-1}$), Si—O—Si (1105), and Si—OR (1060 $cm^{-1}$). Particularly, two new peaks at 1105 $cm^{-1}$ and 1060 $cm^{-1}$ (Si—O) provided evidence for the condensation reaction between GO and silanol from hydrolysis of APS. Furthermore, the functionalized graphene showed decreases in C=O and C—O stretch peak intensities, confirming the deoxygenation of the graphene sheets from the reduction reaction of GO. The occurrences of reactions were further supported by the disappearance of the peak at 3378 $cm^{-1}$ (—OH) and by the emergence of a new peak at 3351 $cm^{-1}$ (—NH). The presence of these functional groups indicates a successful surface modification of the GO accompanied by some degree of reduction of the carboxyl groups. These results confirm that the chemical reduction and surface functionalization of GO with APS occurs essentially simultaneously.

Figure 3:
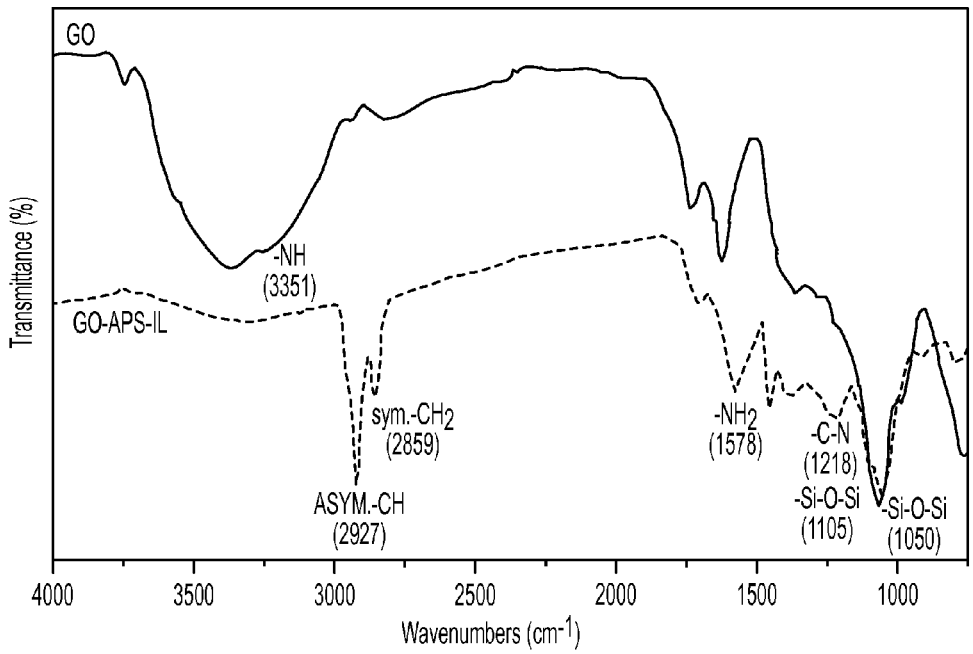
FIG. 3 provides Fourier transform infra-red spectra comparing samples a various stages of preparation according to an embodiment.
Figure 4A:
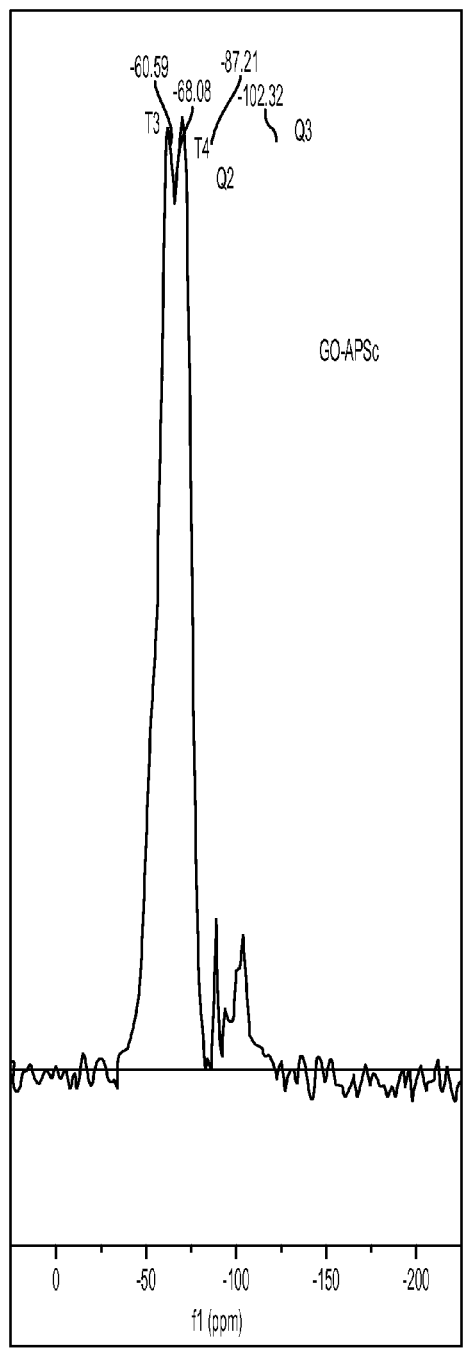
FIGS. 4a and 4b are nuclear magnetic resonance spectra comparing a control with functionalized graphene according to an embodiment.
Figure 4B:
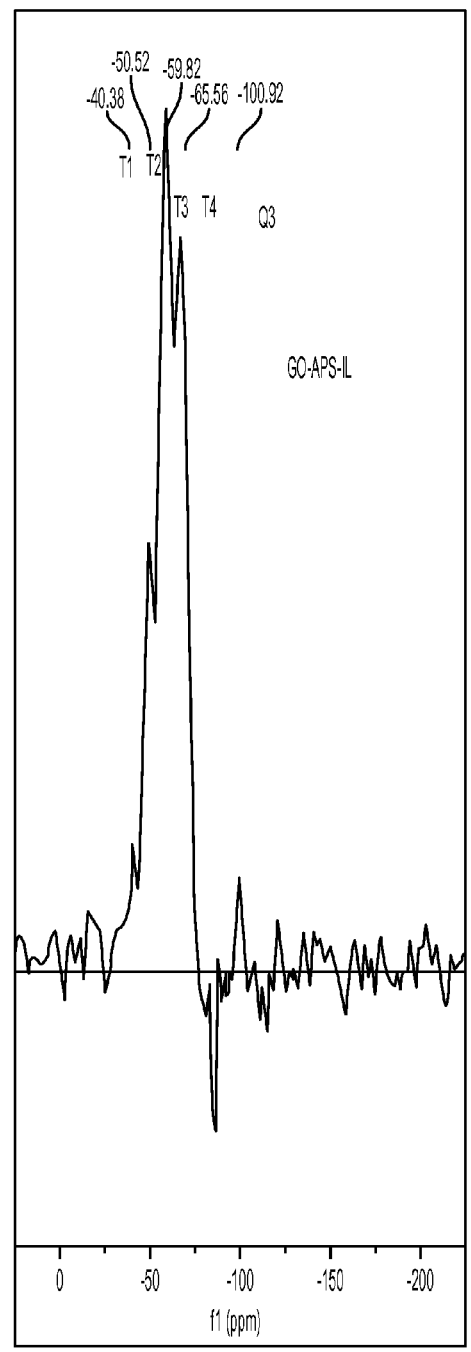

The $_{29}Si$ solid-state NMR spectra in FIGS. 4a and 4b provide information about the structure of the resulting products and hence elucidate the corresponding reaction mechanism during functionalization/reduction with the aid of the IL. By comparing the NMR spectra of GO-APS-IL (FIG. 4b) and the corresponding control sample (GO-APSc) (FIG. 4a), it can be noted that the Q2 site at 87.21 ppm disappeared and two new peaks appeared in GO-APS-IL. The absence of the Q2 peak indicates that the two Si—OH groups in the silanol from hydrolysis of APS reacted with other —OH groups in GO and were completely consumed for chemical functionalization during the treatment. Furthermore, these new sites at 40.38 ppm and 50.52 ppm in GO-APS-IL indicate the presence of more T1-T4 structures (correlation of FIG. 2 with FIGS. 4a and 4b) from condensation reactions of silanol and GO as shown in FIG. 3. The NMR spectra offer direct support for the effect of the IL on chemical functionalization of GO. The improved exfoliation of GO with the aid of the IL exposed more active hydroxyl and carboxyl groups on the graphene sheets and finally led to high yield of APS grafting.

To further evaluate the surface composition of each type of samples, X-ray photoelectron spectroscopy (XPS) was used to achieve information of surface functional groups. The C 1s XPS spectrum of GO revealed a considerable degree of oxidation with four deconvoluted components, $sp^2$-hybridized C—C in aromatic ring (284.5 eV), C—OH (286.4 eV), C—O—C (287.4 eV), and C(O)OH (288.6 eV). The atomic percentage of different oxygen containing functional groups was calculated with respect to the total area of the C 1s peak and the results indicated that the C—O bonds (67.87 atom %) from epoxide and hydroxyl groups constituted the majority of oxygen-containing functional groups in GO, while C(O)O bonds (5.04 atom %) from carboxyl groups accounted for only a portion. In contrast, the GO-APS-IL sample exhibited a significant increase in the C—C bonds (65.96% for GO-APS-IL vs. 27.09% for GO) but a decrease in the C—OH bonds and the absence of the C—O—C bonds, indicate deoxygenation of some oxygen containing groups and restoration of the π-conjugated structure in the graphene. Although the O—C=O bonds were abundant in GO-APS-IL, complete exfoliation of graphene sheets probably exposes more surface functional groups and hence makes them easily detectable during the surface survey. The appearance of a π-π* component in GO-APS-IL predicts the restoration of delocalized π-conjugation in the graphene sheets.

The drastic increase of the $sp^2$ C—C bonds in GO-APS-IL over GO-APSc suggests that the restoration of the graphene structure on the graphene surface was more favored in the presence of the IL. Additionally, an emission at 285.8 eV corresponding to C—N was observed in GO-APS-IL, suggesting that more amine groups from APS were grafted onto the graphene sheets in the presence of IL. Furthermore, the carbon-to-oxygen ratio increased after surface functionalization, implying increased elimination of some oxygen-containing groups by reactive consumption during functionalization and more restoration of the $sp^2$ C—C bonds by reduction reaction in the presence of the IL compared to the control. On the other hand, compared to GO-APSc, two distinctive peaks (Si 2p and N 1s) appear from the surface survey of GO-APS-IL that further offer direct support of effective functionalization due to complete exfoliation of graphene sheets with the aid of the IL during the reaction. Specifically, a strong peak of GO-APS-IL at about 102.3 eV for Si 2p confirms that efficient functionalization of graphene occurs under the aid of the IL. The surface survey of GO contains no detectable Si and N peaks, while that of GO-APSc demonstrates very weak Si 2p and N 1s peaks (after local magnification) compared to the corresponding very strong and apparent peaks of Si 2p and N 1s in GO-APS-IL.

Figure 5:
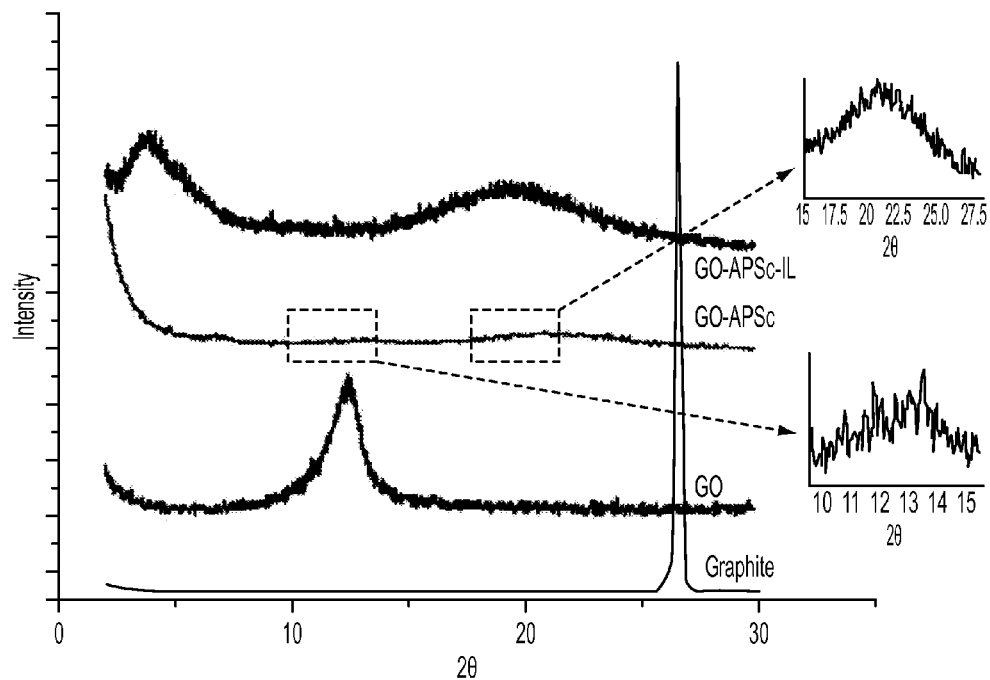
FIG. 5 depicts X-ray diffraction spectra comparing samples a various stages of preparation according to an embodiment.

In the X-ray diffraction spectra (XRD) shown in FIG. 5, pristine graphite exhibited a strong characteristic (002) peak centered at 2θ=26.56° corresponding to a spatial distance of 0.335 nm for the graphene layer stacking. Oxidation of pristine graphite shifted this characteristic peak to a lower angle (2θ=11.74°, d=0.75 nm). The increase in interlayer spacing is due to the intercalation of water molecules between the graphene layers and the attachment of oxygen-containing functional groups on graphene sheets. Silane treatment of GO resulted in further increase in interlayer spacing. GO-APSc exhibited a peak at 13.62° corresponding to an interlayer spacing of 0.65 nm, while GO-APS-IL demonstrated an interlayer spacing of 2.27 nm (2θ=3.88°). The disappearance of the (002) peak attributed to pristine graphite and the appearance of new broad bands in GO-APS-IL indicate that the IL prevented the restacking and aggregation of graphene sheets and maintained the product in the exfoliated state. Furthermore, the evolution of a peak centered at 2θ=11.74° in the XRD spectrum (FIG. 5) also confirms the partial removal of oxygen-containing functional groups in XPS analysis. The appearance of two peaks at 2θ=19.3° (d=0.45 nm) and 21.6° (d=0.40 nm) in GO-APS-IL and GO-APSc further confirmed the partial reduction occurred simultaneously during the chemical functionalization and restructure of the graphene layer after the functionalization. The interlayer spacing of GO-APS-IL was slightly larger than that of GO-APSc, implying the better exfoliation after the treatment and hence difference from the aid of the IL during the chemical functionalization.

Figure 6:
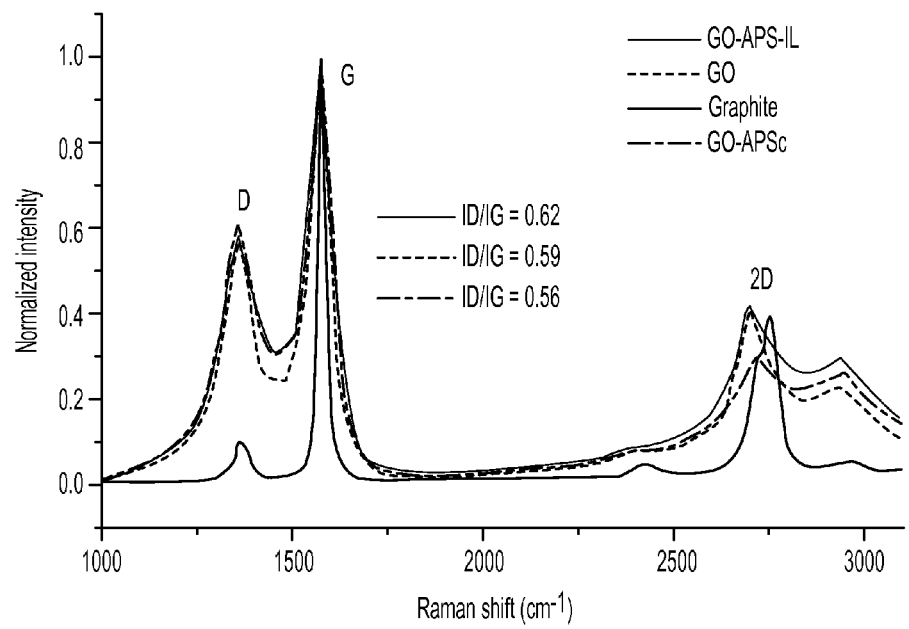
FIG. 6 depicts Raman spectra comparing samples a various stages of preparation according to an embodiment.

Graphene layers were also examined using Raman spectroscopy, the results of which are reproduced in FIG. 6. During the chemical process from pristine graphite to GO, and then to the surface modified graphene, the structure of graphene sheets undergoes rearrangement of carbon atoms in the basal plane. Such structural changes of GO, GO-APSc, and GO-APS-IL may be evaluated by Raman spectroscopy with a laser excitation at 442 nm. Three characteristic bands in the Raman spectrum, 1324 cm$^{-1}$, 1591 cm$^{-1}$, and 2685 cm$^{-1}$, may be used to gauge the apparent structural changes that occur during oxidization and chemical reduction/functionalization compared to pristine graphite. The peak at 1324 cm$^{-1}$, the disorder-induced band (called D band), is related to a breathing mode of k-point phonons of $A_{1g}$ symmetry and usually associated with the $sp_3$ defect sites or flake edges. The sharp peak at 1590 cm$^{-1}$ (called G-band) corresponds to the first-order scattering of the $E_{2g}$ mode, originating from the bond stretching of all $sp_2$-bonded pairs. As shown in FIG. 6, compared to the D band of GO, the D bands for GO-APSc and GO-APS-IL have little red-shift. In contrast to pristine graphite, GO, GO-APSc, and GO-APS-IL all exhibited noticeable Raman shift increases in the D band which became broader due to structural imperfection caused by heterogeneous functional groups on the graphene basal plane. The intensity ratio of the D and G bands is considered to be a measure of the disorder and reflects the relative disorder of structural imperfection. As can be seen in FIG. 6, the intensity ratio of ID/IG increases a small amount from GO to functionalized graphene owing to the enhanced defects from the severe disruption of more functional groups attached. The relatively small difference in ID/IG between GO and functionalized graphene also predicts the unchanged basic sizes of graphene through functionalization. The significantly higher intensity of the G band than that of the D band indicates that the prepared graphene sheets contain few defects and hence are of a high quality of synthesized graphene. The higher-order peak that appeared at 2680-2700 cm$^{-1}$ may be attributed to a 2D band, which results from the two phonon double resonance Raman process. Generally, the intensity of the 2D peak with respect to the D and G peaks is small due to disorder. The shape and position of the 2D peak are characteristic of the number of graphene layers. Typically, deconvolution of the 2D band for the restacked graphene sheets yields two Lorentzian peaks, having characteristic of conventional graphitic materials. Compared to pristine graphite, the 2D peak positions in GO, GO-APSc, and GO-APS-IL shifts to a lower wavenumber by more than 50 cm$^{-1}$. Deconvolution of the 2D bands showed that GO and GO-APS-IL each have a single Lorentzian-fitting peak indicating the characteristic of a single graphene layer. In contrast, two Lorentzian-fitting peaks were noted for GO-APSc and graphite, respectively. The single graphene sheet of GO-APS-IL was mainly due to the complete and effective exfoliation and stabilization of graphene sheets with the aid of the IL during the functionalization/reduction process. In the absence of IL, some of the graphene sheets were possibly restacked during reduction/functionalization in sample preparation.

The layer numbers of GO and functionalized graphene sheets were also examined by transmission electron microscopy and selected area electron diffraction (SAED). SAED patterns of GO and GO-APS-IL revealed perfect hexagonal symmetric structure from graphene diffraction with a beam incident along [0001] direction. The observed average SAED intensity ratio of the GO and GO-APS-IL samples was between 1.5 and 2, suggesting that the {11100} spots appeared to be more intense than the {2100} spots. The size of spots in the SAED is affected by the presence of functional groups. The larger size of the spots indicates a bigger fluctuation of carbon position from the strained C—C bonds caused by functional groups. GO-APS-IL exhibited larger SAED spots than GO, suggesting the presence of more functional groups on the graphene sheets. TEM microscopy revealed that the edges of the suspended graphene sheet of GO tended to fold back, which was possibly due to the heavily oxygenated surface groups. In contrast, the monolayer of GO-APS-IL did not show any wrapping, and multilayer graphenes of GO-APSc were significantly differentiated from monolayer graphene of GO-APS-IL.

Based on the results obtained, the illustration of FIG. 1 is indicative of a proposed mechanism for the pH-triggered electrochemically interacted exfoliation to elucidate the IL-assisted functionalization and reduction of graphite oxide. First, the cationic IL may be strongly attracted by the electron negative π bonds of graphene sheets. Second, the probable deprotonation of surface functional groups on GO graphene sheets in the solution may also attract cations in the IL and render them form a cluster of charges on the GO graphene sheets by the Brownian motion of cations. As a result, the IL may be strongly adsorbed on the graphene sheets, forming a charged diffuse layer. These charged layers may produce the Coulomb repulsion forces between charged graphene sheets and hence make oxidized graphene sheets easily separate when ultrasonication is applied to promote the mobility of cations and overcome the strong van der Waals interactions between the graphene sheets. On the other hand, after the functionalization/reduction, the high dielectric constant of the IL provides shielding for the π-π restacking interactions and the van der Waals interactions. The IL may also act as a stabilizer to prevent the agglomeration of the graphene sheets during the functionalization. The adsorbed IL can be easily removed due to the water-soluble nature of the ILs compared with other surfactants or stabilizers. Therefore, the produced graphene may retain its unique intrinsic properties. In general, the physicochemical properties of the ILs, especially their hydrophilicity and hydrophobicity, can easily be tuned by varying alkyl appendages of the cations and/or counteranions. Therefore, ILs can greatly assist the accessibility of the hydroxyl and carboxyl groups on the surfaces of graphene for functionalization reactions through excellent exfoliation and wetting of graphene, thereby enhancing its functionality and organophilic dispersibility.

The example functionalized graphene produced as discussed herein using ionic liquids showed improved organophilicity, good wettability, and improved interfacial interactions, as well as significant resistance to thermal degradation relative to conventionally prepared graphene. This shows that ionic liquids may be used as a reaction medium to promote chemical functionalization of graphene through electrochemically interacted exfoliation of graphene sheets. In addition, by manipulating the chemical groups attached during the functionalization, the functionalized graphene sheets may present different solubility behavior in organic solvent or in polymer blends, and hence serve as a processing aid for engineering interfacial compatibility between graphene and a variety of matrixes or substrates.

EXAMPLES

Example 1

Preparation of Graphite Oxide

Powdered natural graphite flakes (5 g, Sigma-Aldrich) were thoroughly ground in three grinding cycles of about 30 minutes each, with 1-butyl-3-methylimidazolium chloride (10 g, ≥95%, Sigma-Aldrich) using a mortar and pestle. The resulting gel-like paste was repeatedly washed with excess amounts of ultrapure Milli-Q® water and then filtered through standard filter paper with a Büchner funnel. The obtained graphite powder was dried under a hood at least one day at room temperature.

The dried graphite powder was further treated to prepare graphite oxide according to a modified Hummers method. For this procedure, the pretreated graphite powder (2 g) was added to cold concentrated $H_2SO_4$ (0° C., 46 mL, 98.08%, J. T. Baker). While keeping the reaction temperature less than 10° C., $NaNO_3$ (2 g, EMD Chemicals) and $KMnO_4$ (6 g, J. T. Baker) were slowly added into the $H_2SO_4$ suspension until completely dissolved. After 30 minutes of stirring in an ice-water bath, the temperature of the mixture was increased to 35±3° C. and the reaction was continued for another hour. Subsequently, 100 mL ultrapure water was gradually added to the mixture, an exothermic reaction that increased the temperature to 98° C. The mixture was stirred for 30 minutes followed by adding 500 mL of ultrapure water. Next, 15 mL $H_2O_2$ (30%, J. T. Baker) was added to the mixture, resulting in a bright yellow color along with vigorous bubbling. The mixture was left overnight and the clear supernatant was decanted. The remaining mixture was centrifuged and washed, first with 1 L of 10% HCl (36.5-38%, J. T. Baker) solution, followed by washing with 1 L ultrapure water. The resulting graphite oxide was diluted into 2 L of ultrapure water, yielding a brown dispersion that was subjected to dialysis to completely remove residual salts and acids. The remaining graphite oxide dispersion (1 wt %) was collected by centrifugation.

Example 2

Preparation of Functionalized Graphene from Graphite Oxide

An ethanol solution was prepared by adding 500 mg of ionic liquid trihexyltetradecylphosphonium decanoate (t-HDPD, Sigma-Aldrich, ≥95%) to ethanol (150 mL), and sonicating the solution in a water bath for 15 minutes. Following the sonication, the functionalizing compound 3-aminopropyl triethoxysilane (APS) (99%, 2 g, Fisher Scientific)

was introduced into the ethanol solution, and the pH was adjusted to 5 using acetic acid. A graphite oxide dispersion (100 ml of a 1 wt % dispersion), such as that prepared in Example 1, was added into the mixed ethanol solution and sonicated for 30 minutes using a Branson Digital Sonifier (S450D, 500 W) to exfoliate the graphite oxide and produce graphene oxide. The mixture was refluxed with magnetic stiffing for 24 hours at 80° C. to reduce and functionalize the graphene oxide. The resulting black solution was filtered, and the collected, functionalized graphene solid was first washed several times using ethanol, then washed with ultrapure water. The functionalized graphene was freeze-dried for storage.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one" or "more" or "at" least "one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method for producing functionalized graphene, the method comprising:
    contacting graphite oxide with at least one functionalizing compound in the presence of at least one first ionic liquid to form a mixture;
    sonicating the mixture to form exfoliated graphene oxide; and
    refluxing the exfoliated graphene oxide to form the functionalized graphene.

2. The method of claim 1, wherein the contacting comprises contacting the graphite oxide with the at least one functionalizing compound in the presence of the at least one first ionic liquid and a solvent.

3. The method of claim 2, wherein the contacting comprises contacting the graphite oxide with the at least one functionalizing compound in the presence of the at least one first ionic liquid and the solvent selected from the group consisting of water, toluene, dimethylformamide, xylene, ethanol, and any combination thereof.

4. The method of claim 1, wherein the contacting comprises contacting the graphite oxide with the at least one functionalizing compound in the presence of the at least one first ionic liquid and at least one acid.

5. The method of claim 4, wherein the contacting is performed at a pH of about 4 to about 5.

6. The method of claim 4, wherein the contacting comprises contacting the graphite oxide with the at least one functionalizing compound in the presence of the at least one first ionic liquid and the at least one acid selected from the group consisting of lactic acid, acetic acid, formic acid, citric acid, oxalic acid, uric acid, propionic acid, butyric acid, sorbic acid, tartaric acid, malonic acid, malic acid, maleic acid, succinic acid, fumaric acid, hydrochloric acid, nitric acid, phosphoric acid, and any combination thereof.

7. The method of claim 1, wherein the contacting comprises contacting the graphite oxide with at least one functionalizing compound in the presence of the at least one first ionic liquid, wherein the functionalizing compound is a coupling agent.

8. The method of claim 7, wherein the contacting comprises contacting the graphite oxide with the at least one coupling agent in the presence of the at least one first ionic liquid, wherein the coupling agent comprises a monomer having at least two functional groups.

9. The method of claim 7, wherein the contacting comprises contacting the graphite oxide with the at least one coupling agent selected from the group consisting of a silicon-based coupling agent, a germanium-based coupling agent, and a combination thereof, in the presence of the at least one first ionic liquid.

10. The method of claim 1, wherein the contacting comprises contacting the graphite oxide with the at least one functionalizing compound selected from the group consisting of (3-aminopropyl)trimethoxysilane, 3-glycidoxypropyldimethoxy-methylsilane, (3-mercaptopropyl)trimethoxysilane, 3-(triethoxysilyl)propyl isocyanate, N1-(3-trimethoxysilylpropyl)diethylenetriamine, N-[3-(trimethoxysilyl)propyl]ethylenediamine, and any combination thereof, in the presence of the at least one first ionic liquid.

11. The method of claim 1, wherein the contacting comprises contacting the graphite oxide with the at least one functionalizing compound in the presence of the at least one first ionic liquid selected from the group consisting of imidazolium ions, phosphonium ions, 1-butyl-2,3-dimethylimidazolium chloride, 1-butyl-2,3-dimethylimidazolium tetrafluoroborate, 1-butyl-2,3-dimethylimidazolium hexafluorophosphate, 1-butyl-3-methylimidazolium acetate, 1-butyl-3-methylimidazolium bis(trifluoromethylsulfonyl)imide, 1-butyl-3-methylimidazolium bromide, 1-butyl-3-methylimidazolium dibutyl phosphate, 1-butyl-3-methylimidazolium methanesulfonate, 1-butyl-3-methylimidazolium tetrafluoroborate, 1-ethyl-2,3-dimethylimidazolium tetrafluoroborate, 1-ethyl-2,3-dimethylimidazolium chloride, 1-ethyl-2,3-dimethylimidazolium hexafluorophosphate, 1-ethyl-3-methylimidazolium bromide, 1-ethyl-3-methylimidazolium chloride, 1-ethyl-3-methylimidazolium hexafluorophosphate, 1-ethyl-3-methylimidazolium trifluoromethanesulfonate, 1-hexyl-3-methylimidazolium chloride, 1-hexyl-3-methylimidazolium hexafluorophosphate, 1-hexyl-3-methylimidazolium tetrafluoroborate, 1-hexyl-3-methylimidazolium trifluoromethansulfonate, trihexyltetradecylphosphonium decanoate, trihexyltetradecylphosphonium bis(2,4,4-trimethylpentyl)phosphinate, trihexyltetradecylphosphonium dicyanamide, and any combination thereof.

12. The method of claim 1, wherein refluxing the graphite oxide-solvent mixture comprises refluxing the graphite oxide-solvent mixture at the temperature of at least about 25° C.

13. The method of claim 1, wherein refluxing the graphite oxide-solvent mixture comprises refluxing the graphite oxide-solvent mixture at the temperature of about 25° C. to about 180° C.

14. The method of claim 1, wherein refluxing the graphite oxide-solvent mixture comprises refluxing the graphite oxide-solvent mixture at the pressure of at least about ambient atmospheric pressure.

15. The method of claim 1, wherein refluxing the graphite oxide-solvent mixture comprises refluxing the graphite oxide-solvent mixture at the pressure of about 0.1 MPa to about 1.1 MPa.

16. The method of claim 1, wherein refluxing the graphite oxide-solvent mixture comprises refluxing the graphite oxide-solvent mixture for at least about 0.5 hours.

17. The method of claim 1, wherein refluxing the graphite oxide-solvent mixture comprises refluxing the graphite oxide-solvent mixture for about 0.5 hours to about 72 hours.

18. The method of claim 1, wherein contacting the graphite oxide comprises contacting the graphite oxide prepared by a method comprising:
    comminuting graphite in the presence of a second ionic liquid to produce pre-treated graphite; and
    converting the pre-treated graphite into the graphite oxide.

19. The method of claim 18, wherein comminuting the graphite comprises comminuting the graphite in the presence of the second ionic liquid, wherein the second ionic liquid is the same as the first ionic liquid.

20. The method of claim 18, wherein comminuting the graphite comprises comminuting the graphite in the presence of the second ionic liquid, wherein the second ionic liquid is different from the first ionic liquid.

21. The method of claim 18, wherein the comminuting comprises grinding the graphite.

22. The method of claim 21, wherein the grinding comprises grinding to a size of less than about 50 microns.

23. The method of claim 21, wherein the grinding comprises grinding the graphite with a mortar and pestle.

24. The method of claim 18, wherein the converting comprises oxidizing the pre-treated graphite in the presence of sulfuric acid and potassium permanganate.

25. The method of claim 18, wherein the converting comprises oxidizing the pre-treated graphite in the presence of nitric acid and potassium chlorate.

26. The method of claim 18, wherein the converting comprises oxidizing the pre-treated graphite with dimanganeseheptoxide.

* * * * *